(12) United States Patent
Fleischer et al.

(10) Patent No.: US 7,459,732 B2
(45) Date of Patent: Dec. 2, 2008

(54) GAS-SENSITIVE FIELD-EFFECT TRANSISTOR WITH AIR GAP

(75) Inventors: Maximilian Fleischer, Höhenkirchen (DE); Uwe Lampe, Buxtehude (DE); Hans Meixner, Haar (DE); Roland Pohle, Herdweg (DE); Ralf Schneider, München (DE); Elfriede Simon, München (DE)

(73) Assignee: Micronas GmbH, Freiburg (DE)

( * ) Notice: Subject to any disclaimer, the term of this patent is extended or adjusted under 35 U.S.C. 154(b) by 312 days.

(21) Appl. No.: 11/396,243

(22) Filed: Mar. 31, 2006

(65) Prior Publication Data

US 2006/0260737 A1    Nov. 23, 2006

(30) Foreign Application Priority Data

Mar. 31, 2005    (DE) .................. 10 2005 014 763

(51) Int. Cl.
*H01L 27/108* (2006.01)
(52) U.S. Cl. .............. 257/226; 257/213; 257/234; 257/254; 257/444; 257/E31.001
(58) Field of Classification Search ............. 257/313, 257/226, 234, 254, 444, E31.001
See application file for complete search history.

(56) References Cited

U.S. PATENT DOCUMENTS

| | | | |
|---|---|---|---|
| 3,663,870 A | 5/1972 | Tsutsumi et al. | |
| 4,023,549 A | 5/1977 | Hewitt | |
| 4,151,060 A | 4/1979 | Isenberg | |
| 4,354,308 A | 10/1982 | Shimada et al. | |
| 4,633,704 A | 1/1987 | Tantram et al. | |

(Continued)

FOREIGN PATENT DOCUMENTS

DE    2947050    11/1979

(Continued)

OTHER PUBLICATIONS

Doll et al., "Ein Baukastensystem aus hybriden GasFET-Modulen," ITG-Fachberichte 126: Sensoren-Technologie und Anwendung, VDE Verlag, Berlin, Germany, 1994, pp. 465-470, XP-000874734.

(Continued)

*Primary Examiner*—Evan Pert
*Assistant Examiner*—Tan N Tran
(74) *Attorney, Agent, or Firm*—O'Shea Getz P.C.

(57) ABSTRACT

A gas-sensitive field-effect transistor may be formed from a substrate with a gas-sensitive layer and a transistor processed separately and then assembled. The substrate may be patterned to form spacers by which the height of an air gap between the transistor and the sensitive layer may be adjustable to a relatively precise degree. Formation of the spacers can be achieved by patterning the substrate using material-removal techniques. The height of the spacers may be adjusted in the layer thickness of the gas-sensitive layer and for the transistor fabricated using a CMOS process. Suitable techniques for producing recesses between the spacers include, for example, polishing, cutting, sandblasting, lithographic dry etching, or wet-chemical etching. Suitable materials for the substrate may include, for example, glass, ceramic, aluminum oxide, silicon, or a dimensionally stable polymer. Following preparation of the substrate and the transistor, the two elements of the transistor are joined, for example, using flip-chip methods or adhesive-bonding technology.

9 Claims, 7 Drawing Sheets

U.S. PATENT DOCUMENTS

| | | | |
|---|---|---|---|
| 4,638,346 | A | 1/1987 | Inami et al. |
| 4,792,433 | A | 12/1988 | Katsura et al. |
| 5,635,628 | A | 6/1997 | Fleischer et al. |
| 5,879,527 | A | 3/1999 | Kiesele et al. |
| 6,041,643 | A | 3/2000 | Stokes et al. |
| 6,454,834 | B1 | 9/2002 | Livingstone et al. |
| 6,566,894 | B2 | 5/2003 | Rump |
| 6,935,158 | B2 | 8/2005 | Serina et al. |
| 2002/0092974 | A1 | 7/2002 | Kouznetsov |
| 2004/0112764 | A1 | 6/2004 | Stokes et al. |
| 2004/0133116 | A1 | 7/2004 | Abraham-Fuchs et al. |
| 2005/0035808 | A1 | 2/2005 | Frerichs |

FOREIGN PATENT DOCUMENTS

| | | | |
|---|---|---|---|
| DE | 4028062 | 9/1990 | |
| DE | 4105598 | 9/1992 | |
| DE | 42 39 319 | 4/1993 | 27/414 |
| DE | 4239319 | 4/1993 | |
| DE | 4333875 | 4/1995 | |
| DE | 19534557 | 3/1997 | |
| DE | 19613274 | 10/1997 | |
| DE | 197 08 770 | 8/1998 | |
| DE | 198 49 932 | 5/2000 | 27/403 |
| DE | 199 56 744 | 6/2001 | 27/414 |
| DE | 10245947 | 4/2004 | |
| EP | 0952447 | 4/1998 | |
| EP | 0 947 829 | 10/1999 | |
| EP | 1 059 528 | 5/2000 | |
| EP | 1104884 | 11/2000 | |
| EP | 1 103 808 | 5/2001 | 27/414 |
| EP | 1103809 | 5/2001 | 27/414 |
| EP | 1 176 418 | 1/2002 | |
| JP | 01059049 | 3/1989 | |
| JP | 03131749 | 6/1991 | |
| JP | 03259736 | 11/1991 | |
| WO | WO 94/23288 | 10/1994 | |
| WO | WO 96/01992 | 1/1996 | |
| WO | WO 98/41853 | 9/1998 | |
| WO | WO 03/050526 | 6/2003 | |

OTHER PUBLICATIONS

Pohle et al., "Realization of a New Sensor Concept: Improved CCFET and SGFET Type Gas Sensors in Hybrid Flip-Chip Technology," Transducers, Solid-State Sensors, Actuators and Microsystems, 12$^{th}$ International Conference, Jun. 2003, pp. 135-138.

Doll et al., "Modular System Composed of Hybrid GasFET Modules," ITG-Technical Report 126: Sensors-Technology and Application, VDE Verlag, Berlin, Germany, 1994, pp. 465-470, XP-000874734.

Verification of Translation.

Kienle et al., "Acticated Charcoal and its Industrial Application," Stuttgart : Enke, ISBN 3-432-90881-4, pp. 126 and 162-163, 1980.

Müller et al., "Adsorber for a Low Solvent Load," Intelligent Exhaust Air Cleaning Using Electric Current, Verfahrenstechnik, vol. 37, No. 9, pp. 30-31, 2003.

CCI Charcoal International : Activated Charcoal Textiles Given Uniform Brand Name of Zorflex, MaschinenMarkt, 2004, No. 17, p. 89.

Leu et al., "Evaluation of gas mixtures with different sensitive layers incorporated in hybrid FET structures," Sensors and Actuators B, Elsevier Sequoia, vol. 18-19, 1994, pp. 678-681.

Wöllenstein et al., "Cobalt oxide based gas sensors on silicon substrate for operation at low temperatures," Sensors and Actuators B: Chemical, Elsevier Sequoia, vol. 93, No. 1-3, Aug. 2003, pp. 442-448.

Gergintschew et al., "The capacitively controlled field effect transistor (CCFET) as a new low power gas sensor," Sensors and Actuators B: Chemical, Elsevier Sequoia, vol. 36, No. 1, Oct. 1996, pp. 285-289.

Fleischer et al., "Selective gas detection with high-temperature operated metal oxides using catalytic filters," Sensors and Actuators B, vol. 69, pp. 205-210, 2000.

Pohle et al., "Realization of a New Sensor Concept: Improved CCFET and SGFET Type Gas Sensors in Hybrid Flip-Chip Technology," Transducers, 12$^{th}$ International Conference on Solid-State Sensors, Actuators and Microsystems, Jun. 2003, vol. 1, 9, pp. 135-138.

Peschke et al., "Optimization of Sputtered SnO2 Films as Gas-sensitive Layers for Suspended-gate FETs", Sensors and Actuators B, 1991, pp. 157-160, XP-002379749.

Lampe et al., "GasFET for the detection of reducing gases", Sensors and Actuators B 111-112, 2005, pp. 106-110.

Mizsei et al., "Simultaneous Response of Work Function and Resistivity of some SnO2-based Samples to H2 and H2S", Sensors and Actuators B, 4 (1991), pp. 163-168, XP-002379750.

Doll et al., "Gas detection with work function sensors", Proceedings of the SPIE, SPIE, Bellingham, VA, US, vol. 3539, Nov. 1998, pp. 96-105, XP-002329891.

Paris et al., "57.5: Low Drift Air-Gap CMOS-FET Gas Sensor," Proceedings of IEEE Sensors, vol. 1 of 2, Conf. 1, Jun. 12, 2002, pp. 421-425, 2002, XP010605129, ISBN: 0-7803-7454-1.

Burgmair et al., "Humidity and temperature compensation in work function gas sensor FETs," Sensors and Actuators B, Elsevier Sequoia S.A., Lausanne, CH, vol. 93, No. 1-3, pp. 271-275, 2003.

Burgmair et al., "Field effect transducers for work function gas measurements : device improvements and comparison of performance," Sensors and Actuators B, Elsevier Sequoia S.A., Lausanne, CH, vol. 95, No. 1-3, pp. 183-188, 2003.

Covington, et al. "Combined smart chemFET/resistive sensor array," Proceedings of the IEEE, vol. 2., pp. 1120-1123, 2003.

M. Lehmann, "Nanometre Dimensions in Bio and Gas Sensor Technology", MST News, Mar. 2004, pp. 43-47, XP-002379751.

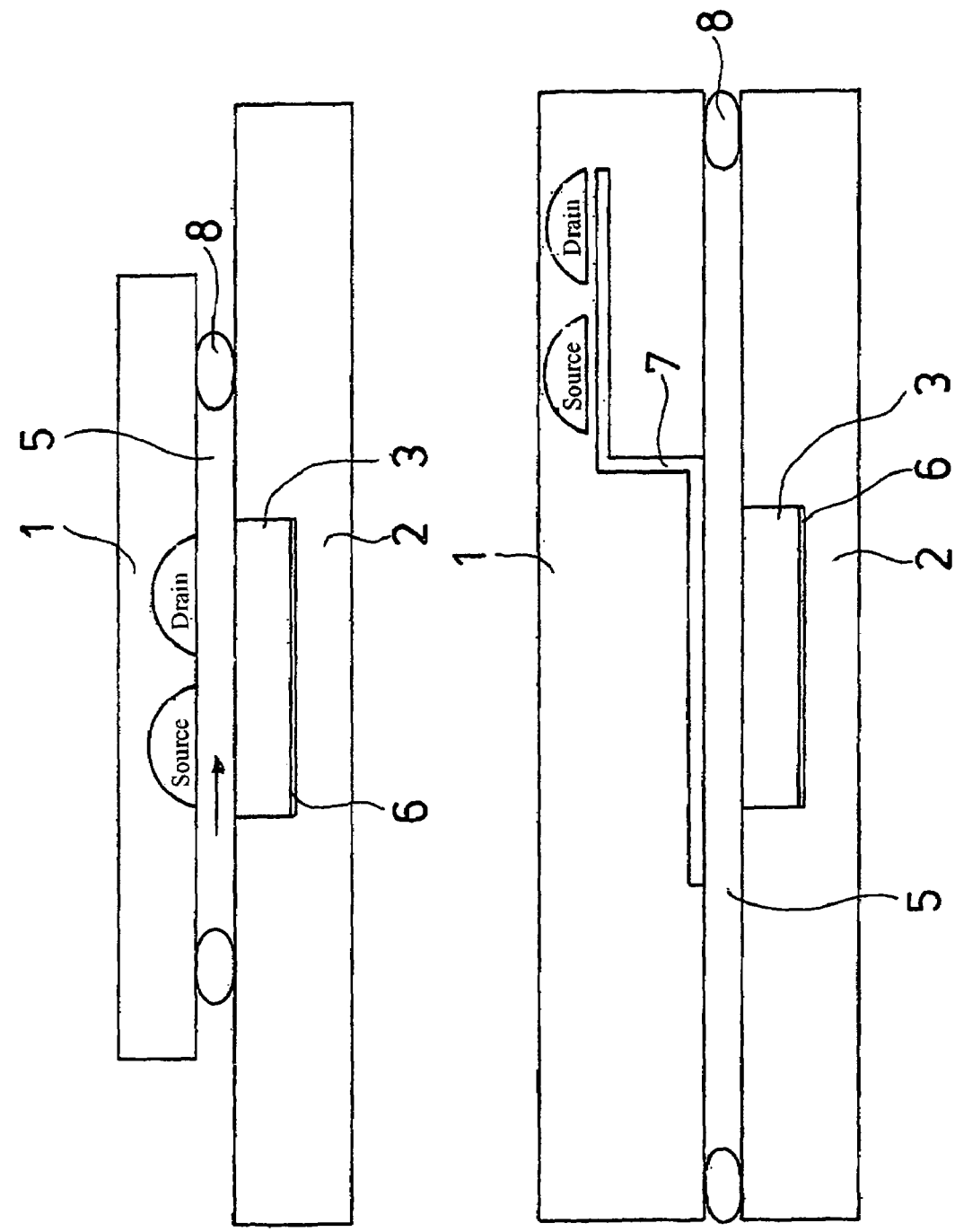

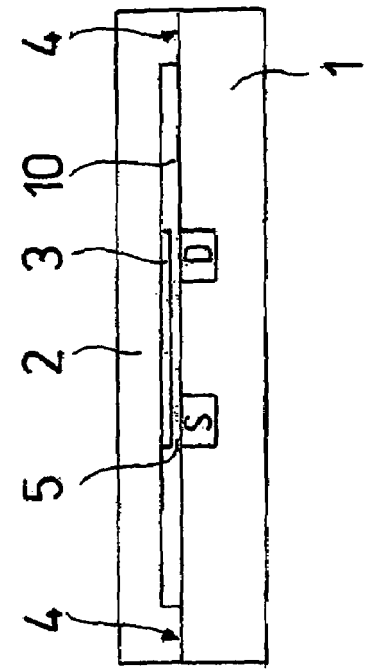
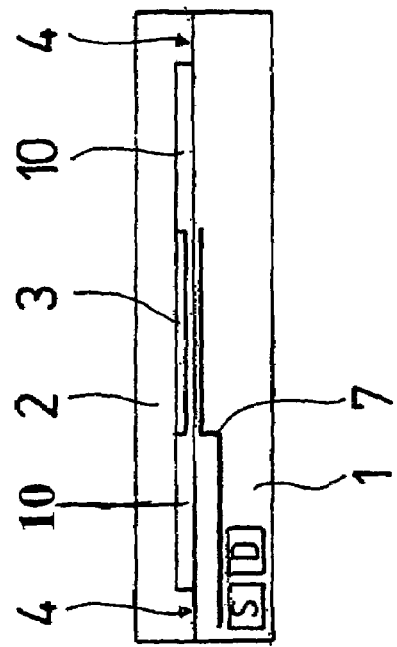
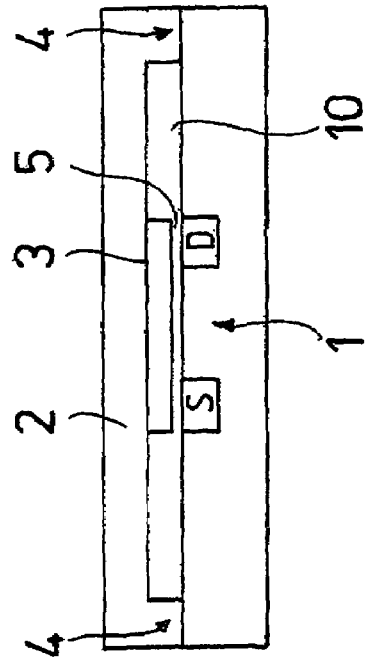
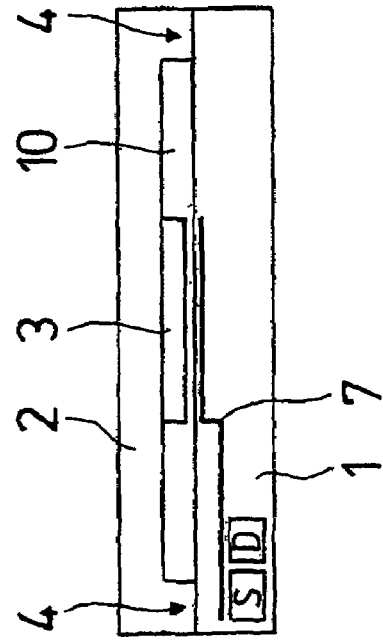

GAS-SENSITIVE FIELD-EFFECT TRANSISTOR WITH AIR GAP

PRIORITY INFORMATION

This patent application claims priority from German patent application 10 2005 014 763.1 filed Mar. 31, 2005, which is hereby incorporated by reference.

BACKGROUND OF THE INVENTION

The invention relates in general to gas sensors and in particular to a gas-sensitive field-effect transistor with an air gap.

The functional principle of gas sensors based on field-effect transistors is known. When compared with other gas sensor technologies, this principle offers a number of advantages, in particular, a wide field of application as well as relatively low production and operating costs. The embodiments of the transistor known as suspended gate field effect transistor (SGFET) and capacitively controlled field effect transistor (CCFET) are especially advantageous. They are characterized by an air gap between a gate electrode and a transistor structure. The gas to be detected is diffused through the air gap and absorbed on a gas-sensitive layer. As a result, a change in potential is generated in the gas-sensitive layer which induces a change in the drain to source current within the transistor structure.

Precise adjustment of the sensitive layer in relation to the transistor structure is a desired parameter in the gas sensor. Accurate control of the air gap height is desirable since the coupling capacity of the gas sensor is directly correlated with the strength the of electrical signal indicative of the amount of detected gas provided by the gas sensor. Since the height of the air gap between the gate electrode and the channel region determines to a large extent the coupling capacity of the potential change induced by the gas absorption, particular attention is typically devoted in the fabrication of the gas sensor to the relatively precise formation of the air gap. Such precise adjustment of the air gap enables the reproducibility of the response characteristic and the sensitivity of the gas sensor, and also improves the bandwidth of the to-be-detected gas concentrations of the sensor.

The thickness of the sensitive layer employed is generally based on the type of gas-sensitive material and the gas to be detected. The desired layer thickness may differ for different layer materials, and care must be taken that this factor is incorporated as necessary into the dimensioning of the air gap.

A suitable method for producing various layer thicknesses is described, for example, in German patent DE19956744. This prior art patent discloses a structure using hybrid flip-chip technology having a field-effect transistor based on a silicon component that incorporates a gas guide channel and a large-area sensitive layer. As a result, the desired clearance or air gap between the silicon component and the substrate is created automatically. The gap is then adjusted on a controlled basis by varying the height of flip-chip bumps.

The disadvantages of known methods of fabricating such gas sensors include the risk of damaging the sensitive layer during fabrication or of the sensor material intruding into the air gap, which factors can lead to the diffusion channel being plugged, or to electrical short circuits.

FIG. 7 is a cross-sectional illustration of a prior art SGFET 1 that performs gas detection, along with the associated electrical circuitry. A gas-sensitive layer 3 is included with a gate electrode 6 in a carrier substrate 2. When a target gas diffuses through an air gap 5 onto the gas-sensitive layer 3, the result is a change in the work function and a change in potential. This potential or potential change couples to the channel region of the transistor 1 between the source and the drain, resulting in a change in the drain to source current IDS. The height of the air gap can be adjusted by the shape of the polymer bumps 8.

What is needed is a gas-sensitive field-effect transistor and a method of fabricating such a transistor to adjust the height of an air gap within the gas-sensitive field-effect transistor.

SUMMARY OF THE INVENTION

According to an aspect of the invention, a substrate with a gas-sensitive layer and a transistor are processed separately from each other before subsequent assembly. The substrate is patterned to form spacers by which the height of an air gap between the transistor and the sensitive layer.

When employing a relatively greater layer thickness for the gas-sensitive layer, formation of the spacers can be achieved by patterning the substrate using material-removal techniques. The spacers ensure a relatively precise adjustment of a desired air gap. The height of the spacers may be adjusted in the layer thickness of the gas-sensitive layer and for the transistor fabricated using a CMOS process. Known techniques are suitable for producing recesses between the spacers, such as, for example, polishing, cutting, sandblasting, lithographic dry etching, or wet-chemical etching. Suitable materials for the substrate may include, for example, glass, ceramic, aluminum oxide, silicon, or a dimensionally stable polymer. When employing thin films as the gas-sensitive layer in a thickness range of a few micrometers or nanometers, the spacers may be created by material deposition implemented, for example, by cathode sputtering, vapor deposition or spray coating. The recesses between the spacers located in the edge region of the substrate can be adjusted according to the layer thickness of the gas-sensitive layer. If material removal techniques are used, such as polishing or sandblasting, then the expected precision is ±1 µm. It may be possible to improve on this result through a post-treatment by a thin-film structure. As a result, it is possible to achieve precisions in the nanometer range.

Following these preparatory measures for both the substrate and the transistor, the two elements of the gas-sensitive field-effect transistor are joined by a suitable joining technology such as, for example, flip-chip methods or adhesive-bonding technology. The use of relatively thick layers makes possible applications of sensor arrangements where multiple sensors are represented on one substrate such that, for example, complex procedures, such as the detection of conflagration gas or the monitoring of ambient air quality can be achieved.

These and other objects, features and advantages of the present invention will become more apparent in light of the following detailed description of preferred embodiments thereof, as illustrated in the accompanying drawings.

BRIEF DESCRIPTION OF THE DRAWINGS

FIG. 1 is a cross-sectional illustration of an SGFET;

FIG. 2 is a cross-sectional illustration of a CCFET;

FIGS. 3 and 4 are cross-sectional illustrations of an SGFET having a constant air gap height despite the varying layer thickness of the gas-sensitive layer;

FIGS. 5 and 6 are cross-section illustrations of a CCFET having a constant air gap height despite the varying layer thickness;

DETAILED DESCRIPTION OF THE INVENTION

Figure 7:
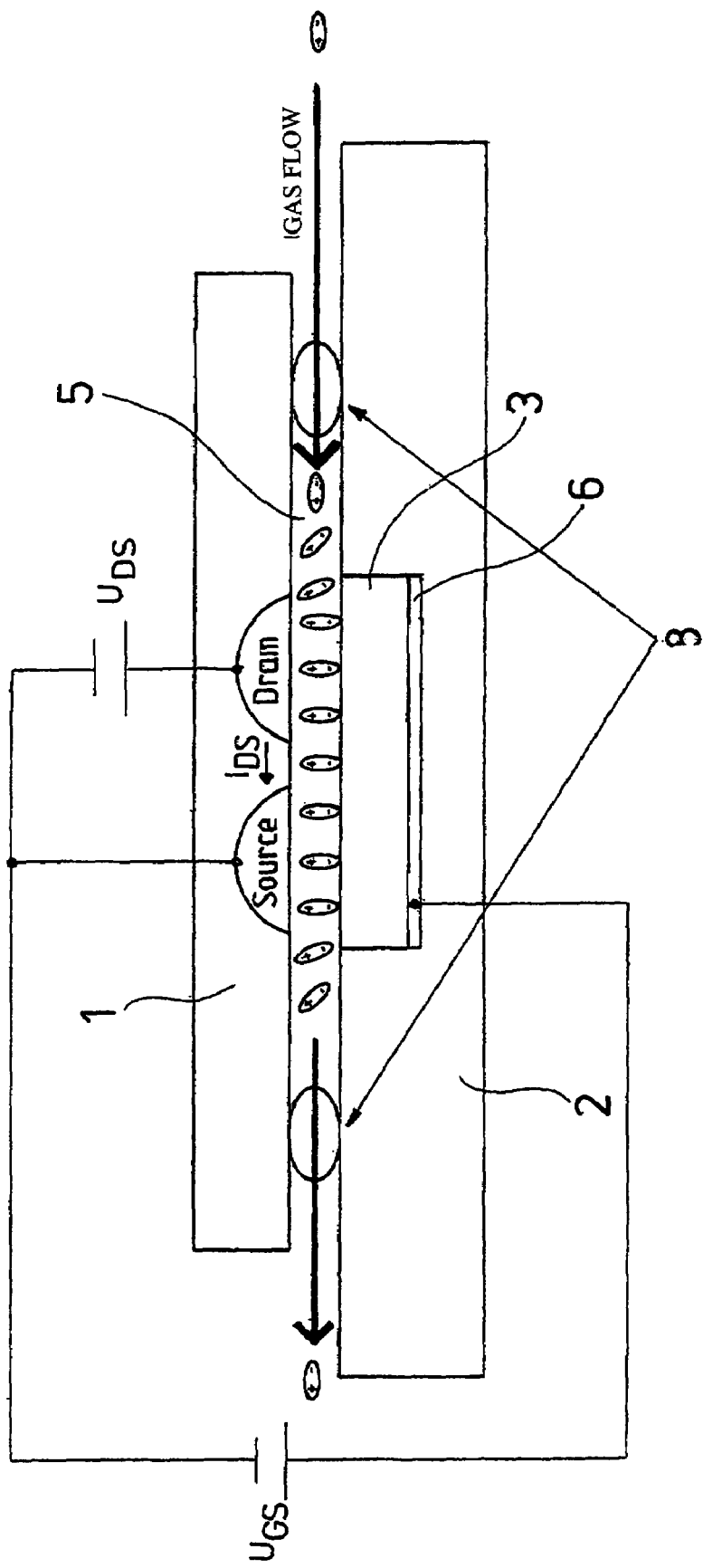
FIG. 7 is a cross-sectional illustration of a prior art SGFET together with a schematic diagram illustration of associated electrical circuitry.

FIG. 7 illustrates a prior art SGFET 1. The diffusion of a target gas through an air gap 5, represented by polarizable oval particles, generates on a gas-sensitive layer 3 a certain potential which couples to the channel of the SGFET 1 and modifies the current between the source and the drain ($I_{DS}$). The gas-sensitive layer 3 is connected to a gate electrode 6. The two tappable voltages lie between the drain and the source ($U_{DS}$), and between the gate electrode 6 and the source ($U_{GS}$).

FIGS. 1-6 provide an overall view of an aspect of the gas-sensitive field-effect transistor of the present invention, with emphasis on the formation of spacers 4 on the substrate 2. If the surface precision requirements of the gas-sensitive layer 3 are relatively low, then the recess of the gas-sensitive layer 3 incorporated into the carrier substrate 2, as illustrated in FIGS. 1 and 2, can be filled in completely such that this layer 3 closes flush with the substrate surface. FIG. 1 illustrates the structure in the suspended gate (SG) field-effect transistor, while FIG. 2 illustrates the structure in a capacitively controlled (CC) field-effect transistor. In each case the height of the air gap 5 is set by flip-chip or polymer bumps 8. A transistor portion comprising source and drain terminals, along with a gate electrode 6, are also illustrated in FIGS. 1 and 2. The transistor of FIG. 2 has a floating electrode 7 that is at least partially disposed over the recess and is laterally disposed away from the recess and over to the drain and source terminals.

FIGS. 3-6 illustrate an alternative approach to forming a relatively precise air gap 5 in an SGFET (FIGS. 3-4) or in a CCFET (FIGS. 5-6). The carrier substrate 2 has a recess 10 which is at least as large as the planar extent of the sensitive layer 3. Spacers 4 are formed in the edge region of the substrate 2 to separate the sensitive layer 3 from the channel region of the transistor 1 when the transistor 1 is mounted on the spacers 4. The overall depth of the recess 10 corresponds to the height of the spacers 4 as they project upward above the base of the recess 10. FIGS. 3-6 each illustrate a substrate 2 which is oriented with the recess 10 facing downward.

Figure 16:
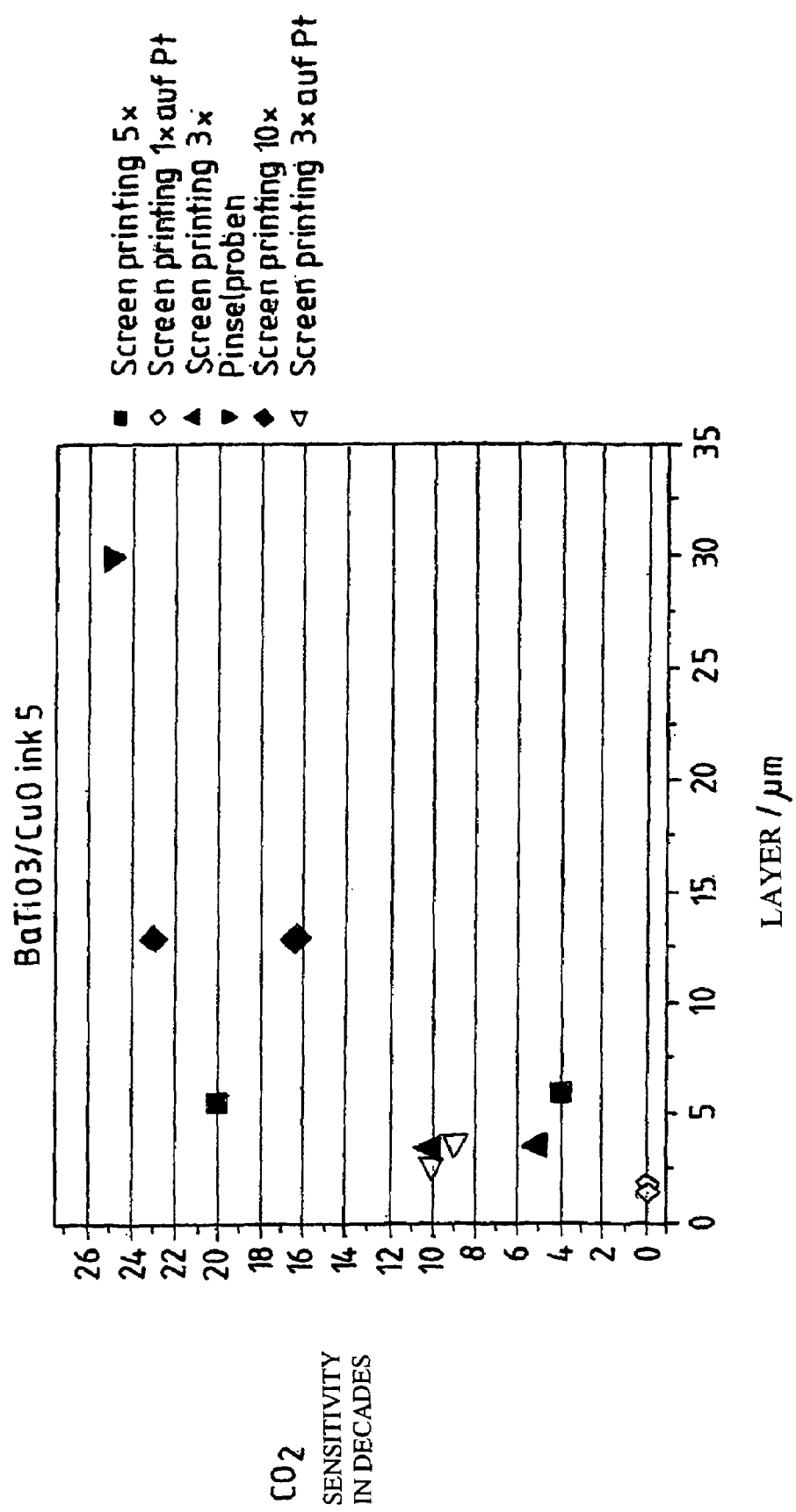
FIG. 16 is a graph of the layer thickness of a gas-sensitive layer versus carbon dioxide sensitivity.

FIG. 16 is a graph illustrating the relationships between the layer thickness of gas-sensitive layers and the corresponding carbon dioxide sensitivity, using an example of a barium titanate/copper oxide system. The sensitivity plotted on the vertical axis is presented in decades. Various standardized methods are plotted on the graph and are listed once or twice as indicated by the symbols. It is evident that a desired or preferred sensitivity for $CO_2$ is obtained for certain detection methods with relatively larger layer thickness.

In connection with the adjustment of a more precisely specified air gap 5 versus that of the prior art, the invention provides the advantages of relatively precise positioning of the sensitive layer 3 relative to the transistor 1 along with improved reproducibility. The result is improved reading of the electrical signal and an increase in the selectivity due to the relatively precise adjustment of the air gap 5.

Possible implementation variants of the fabrication process are described in connection with FIGS. 3-6. To pattern the substrate 2, material removal is effected by etching the photo-patternable glass. The entire surface of this glass may be covered with a light-sensitive photoresist. The relevant regions are exposed with a mask and the resist is developed. The glass is exposed again and the remaining resist is removed. The exposed areas between the spacers 4 are etched out to the required depth. Sandblasting may be used to pattern the substrate 2 by material removal. The surface of the material may be covered with light-sensitive photoresist. These regions are exposed with a mask and the resist is developed. The areas between the spacers 4 are open and are lowered by the sandblasting process to the desired depth. Patterning of the substrate 2 may be performed by polishing or cutting. The ceramic may be polished or cut in stages in a cross structure to the required depth. Patterning of the substrate 2 may be performed by deposition of material to form the spacers 4 using cathode sputtering, vapor deposition, or spray coating. The surface of the substrate 2 may be covered with a light-sensitive photoresist. The appropriate areas are exposed with the mask and the resist is developed. The locations for the spacers remain open. Gold, platinum, or other metals may be deposited up to the specified height. The unwanted material is then removed by stripping off the photoresist (lift-off process).

Suitable substrate materials include, for example, ceramic, glass, silicon, or glass-fiber-reinforced resin.

Figure 8:
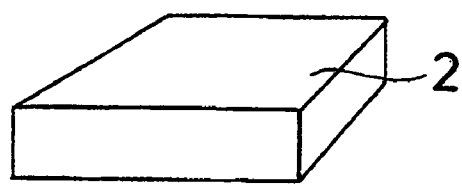
FIGS. 8-11 are perspective views of a substrate through various processing steps, including polishing, subsequent coating with the sensitive layer, then subsequent capping with the transistor.
Figure 9:
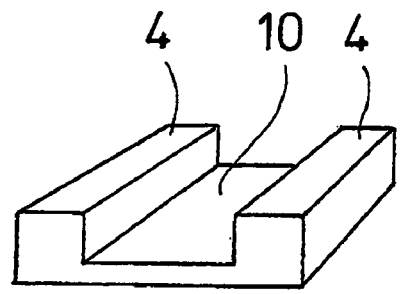
Figure 10:
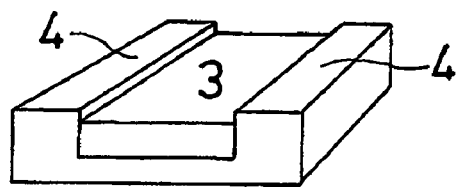
Figure 11:
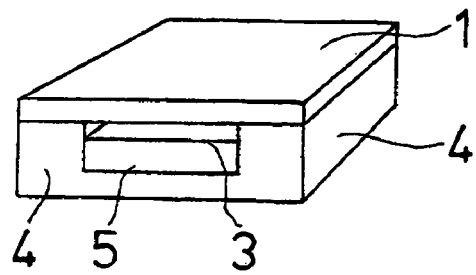
Figure 12:
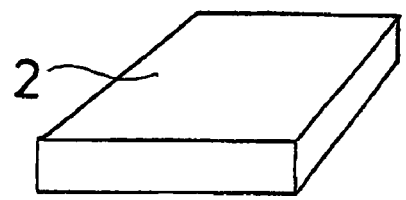
FIGS. 12-15 are perspective views of a substrate through various processing steps in a method of producing recesses, for example, by sandblasting.
Figure 13:
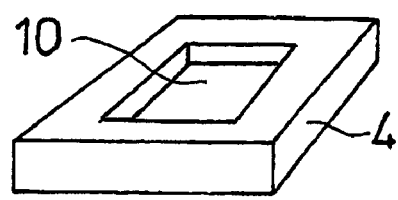
Figure 14:
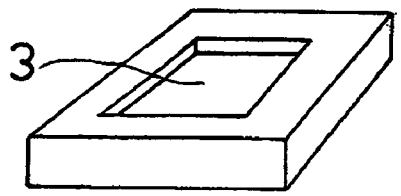
Figure 15:
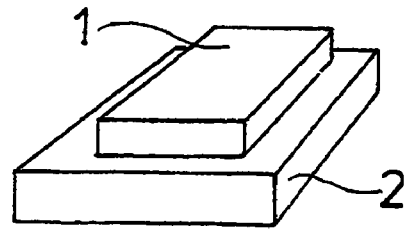

With respect to FIGS. 8-11, starting with an untreated substrate 2 as illustrated in FIG. 8, the recess 10 may be formed in the substrate 2 by a polishing process. The recess 10 is filled, as illustrated in FIG. 10, with the sensitive layer 3, the longitudinally extending spacers 4 serving as the frame. In FIG. 11, an air gap 5 having a relatively precise gap width is present when the recess 10 between the transistor 1 and the gas-sensitive layer 3 is capped. Another variant is illustrated in FIGS. 12-15, where, instead of polishing or cutting, the techniques of sandblasting, lithographic dry etching, or wet-chemical etching are employed. Starting from FIG. 12 with the untreated substrate 2, FIG. 13 illustrates a recess 10 surrounded by spacers 4. In FIG. 14, the recess 10 is filled in with the appropriate sensitive layer 3 to the appropriate thickness such that an air gap 5 of relatively precise gap thickness is formed after flip-chip mounting of the transistor 1. In a system illustrated in FIG. 15, the gas diffusion is effected either through porous sub-regions of the substrate 2 or of the transistor 1, or through macroscopically carved-out gas diffusion passages.

Figure 17:
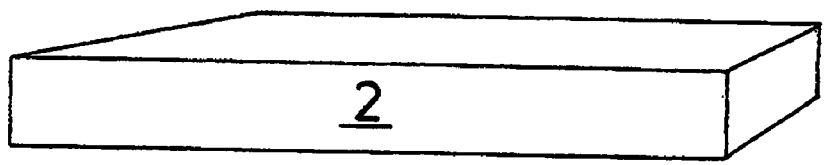
FIGS. 17-20 are perspective views of a substrate through various processing steps in which three recesses of varying depth are incorporated into a single substrate, three gas-sensitive layers of varying thickness are deposited, and the transistor is mounted on the sensor arrangement with the spacers while maintaining an air gap.
Figure 18:
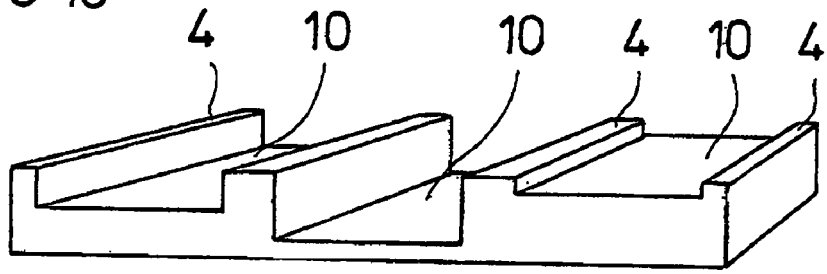
Figure 19:
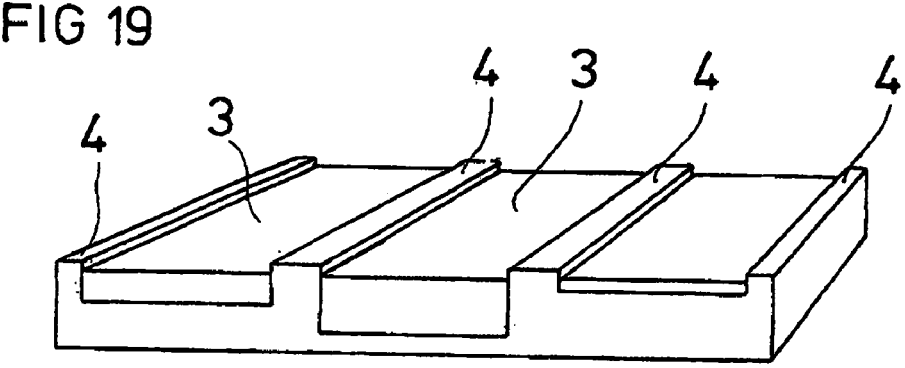
Figure 20:
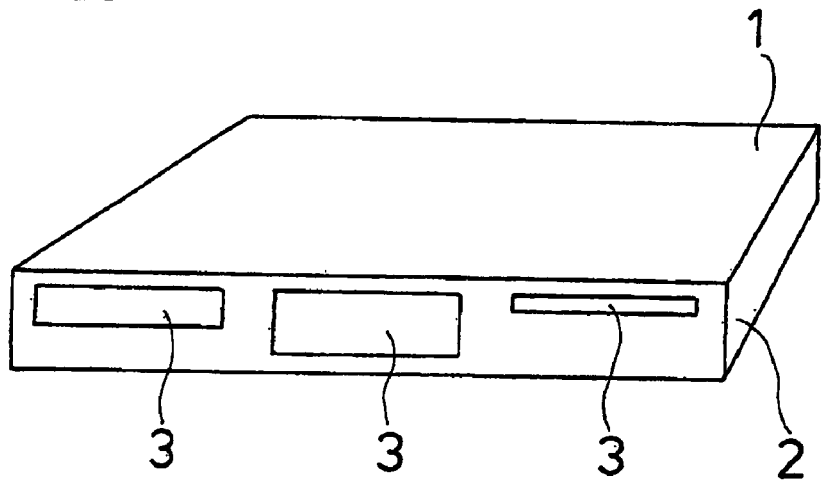

FIGS. 17-20 illustrate a similar sequence, where, starting from an untreated substrate 2 in FIG. 17, several different recesses 10 are carved out. These recesses 10 may be filled with sensitive layer material, either completely or partially, such that the formation of a specified air gap 5 depends on the filling level of the recess 10, or on the flip-chip bump 8, as illustrated in FIG. 7. The arrangement illustrated in FIG. 20 contains three sensors, although FIG. 20 does not illustrate the three corresponding read-out transistors.

Figure 21:
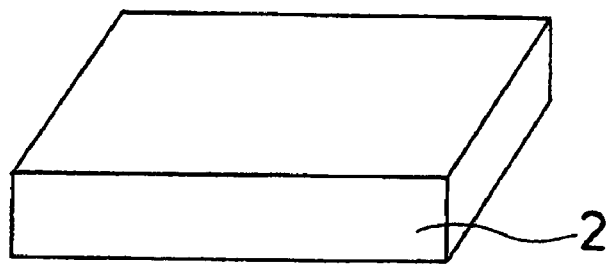
FIGS. 21-24 are perspective views of a substrate through various processing steps starting with an untreated substrate, a patterned substrate is formed with spacers at the corners of the planar substrate, the deposited sensitive layer is formed, and the corresponding structure with the transistor mounted as a cap is formed.
Figure 22:
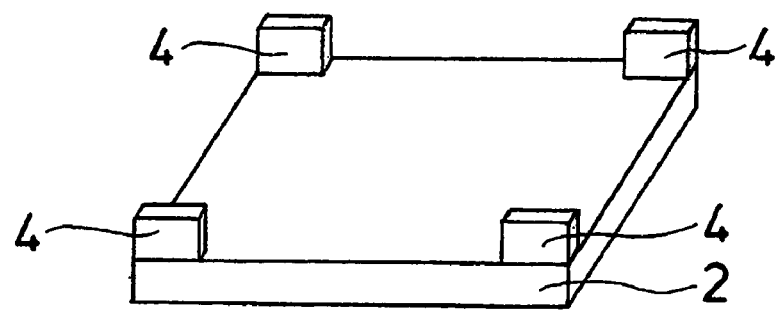

FIG. 21 illustrates a substrate 2, and FIG. 22 illustrates the substrate 2 after patterning to form a plurality of spacers 4, where the material can be, for example, ceramic or glass. The thickness of the sensitive layer 3 directly determines the depth of the recess or the height of the structures representing the spacers 4. In the case of relatively thick layers, removal of material proceeding into the substrate may be implemented. In the case of thin layers to be deposited, addition of material is effected, where, for example, a metal such as gold, nickel, or chromium, is deposited, for example, by cathode sputtering at the sites of the spacers 4. In both cases, raised elements which act as the spacers 4 are formed at the corners of the substrate 2.

Figure 23:
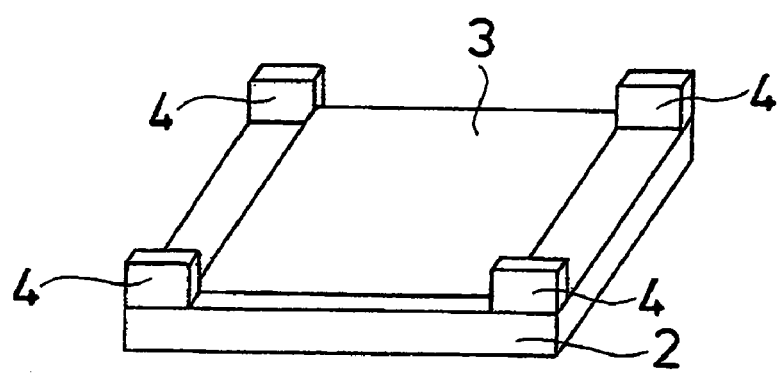
Figure 24:
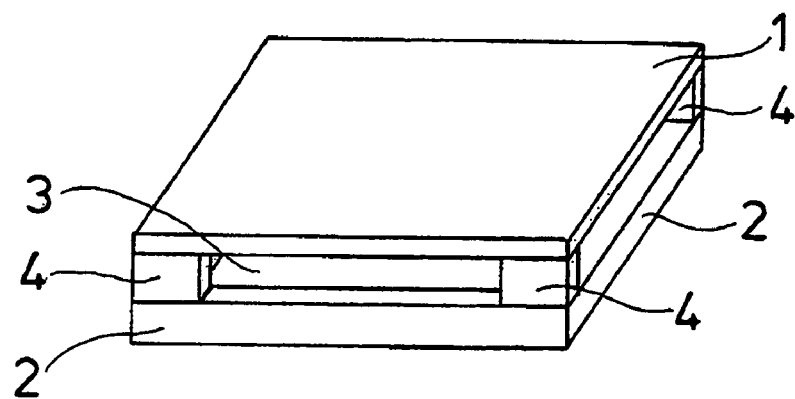

The patterned substrate 2 with gas-sensitive layer is illustrated in FIG. 23, once again the recess 10 is partially filled with the sensitive layer 3. The spacers 4 project beyond the layer 3. As illustrated in FIG. 23, the transistor 1 is mounted accordingly when the arrangement is capped using the flip-chip technique. The desired air gap 5 is created between the sensitive layer 3 and the transistor 1, and the air gap can be produced with precisely formed uniform spacers 4.

Although the present invention has been illustrated and described with respect to several preferred embodiments thereof, various changes, omissions and additions to the form and detail thereof, may be made therein, without departing from the spirit and scope of the invention.

What is claimed is:

1. A gas-sensitive field-effect transistor, comprising:
   a substrate having a surface and recess formed in the surface;
   a transistor having drain and source terminals;
   a plurality of spacers disposed on the substrate surface; and
   a gas-sensitive layer disposed within the recess, the gas-sensitive layer having an upper surface and having a thickness extending above the surface less than a height of the plurality of spacers,
   where the transistor is attached over the gas-sensitive layer onto the spacers to form an air gap between the transistor and the substrate.

2. The transistor of claim 1, where the substrate surface is planar.

3. The transistor of claim 2, where the upper surface of the gas-sensitive layer comprises a planar surface, where the planar upper surface of the gas-sensitive layer is even with the planar surface of the substrate.

4. The transistor of claim 1, where the substrate comprises one of the materials from the group comprising glass, photo-patternable glass, silicon, ceramic, metal, and plastic.

5. The transistor of claim 1, where the recess has a depth at least equal to the height of the plurality of spacers.

6. The transistor of claim 1, further comprising a plurality of recesses formed in the substrate.

7. The transistor of claim 6, where each of the plurality of recesses has a gas-sensitive layer disposed therein.

8. The transistor of claim 6, where the plurality of recesses have varying depths within the substrate.

9. The transistor of claim 8, where the varying depths of the plurality of recesses correspond to thicknesses of the associated gas-sensitive layers such that air gaps of the same height are present for all sensitive layers.

* * * * *

UNITED STATES PATENT AND TRADEMARK OFFICE
CERTIFICATE OF CORRECTION

PATENT NO. : 7,459,732 B2
APPLICATION NO. : 11/396243
DATED : December 2, 2008
INVENTOR(S) : Fleischer et al.

It is certified that error appears in the above-identified patent and that said Letters Patent is hereby corrected as shown below:

Column 1
Line 32, delete "strength the of" and insert --strength of the--

Column 3
Line 63, delete "Spaces" and insert --The spacers--

Signed and Sealed this

Thirteenth Day of January, 2009

JON W. DUDAS
*Director of the United States Patent and Trademark Office*